(12) United States Patent
Tanaka et al.

(10) Patent No.: US 9,488,664 B2
(45) Date of Patent: Nov. 8, 2016

(54) DIAGNOSTIC AGENT FOR TUMOR

(71) Applicant: SBI Pharmaceuticals Co., Ltd., Minato-ku, Tokyo (JP)

(72) Inventors: Tohru Tanaka, Tokyo (JP); Kiwamu Takahashi, Tokyo (JP); Motowo Nakajima, Minato-ku (JP); Fuminori Abe, Tokyo (JP); Masahiro Ishizuka, Tokyo (JP); Urara Ota, Tokyo (JP)

(73) Assignee: SBI Pharmaceuticals Co., Ltd., Tokyo (JP)

( * ) Notice: Subject to any disclaimer, the term of this patent is extended or adjusted under 35 U.S.C. 154(b) by 0 days.

(21) Appl. No.: 14/374,043

(22) PCT Filed: Jan. 15, 2013

(86) PCT No.: PCT/JP2013/000117
§ 371 (c)(1),
(2) Date: Jul. 23, 2014

(87) PCT Pub. No.: WO2013/111528
PCT Pub. Date: Aug. 1, 2013

(65) Prior Publication Data
US 2015/0031013 A1   Jan. 29, 2015

(30) Foreign Application Priority Data

Jan. 25, 2012 (JP) ................. 2012-013497

(51) Int. Cl.
*A61K 31/195* (2006.01)
*G01N 33/72* (2006.01)
*G01N 33/574* (2006.01)
*G01N 33/70* (2006.01)
*A61K 49/00* (2006.01)

(52) U.S. Cl.
CPC ........... *G01N 33/72* (2013.01); *A61K 49/0036* (2013.01); *G01N 33/574* (2013.01); *G01N 33/70* (2013.01); *G01N 2800/7028* (2013.01)

(58) Field of Classification Search
USPC ....................................... 514/561
See application file for complete search history.

(56) References Cited

U.S. PATENT DOCUMENTS

| | | | |
|---|---|---|---|
| 4,938,949 A | 7/1990 | Borch et al. | |
| 2008/0010871 A1 | 1/2008 | Holmes et al. | |
| 2008/0108701 A1* | 5/2008 | Okura et al. | 514/561 |
| 2011/0004098 A1* | 1/2011 | Danikas et al. | 600/435 |
| 2011/0033386 A1 | 2/2011 | Inoue et al. | |

FOREIGN PATENT DOCUMENTS

| | | |
|---|---|---|
| JP | 04-500676 A | 2/1992 |
| JP | 05-310576 A | 11/1993 |
| JP | 11-012197 A | 1/1999 |
| JP | 11-501914 A | 2/1999 |
| JP | 2000-207357 A | 7/2000 |
| JP | 2006-124372 A | 5/2006 |
| JP | 2007-268229 A | 10/2007 |
| JP | 2009-524415 A | 7/2009 |
| JP | 2011-016753 A | 1/2011 |
| WO | WO 96/28412 A1 | 9/1996 |
| WO | WO 98/57668 A1 | 12/1998 |
| WO | WO 2007/085084 A1 | 8/2007 |
| WO | WO 2009/130893 A1 | 10/2009 |
| WO | WO 2011/161933 A1 | 12/2011 |

OTHER PUBLICATIONS

Lippert et al. CAS: 143: 22244, 2005.*
Ishizuka et al., "Novel development of 5-aminolevurinic acid (ALA) in cancer diagnoses and therapy," International Immunopharmacology, 2011, 11:358-365.

* cited by examiner

Primary Examiner — Rei-Tsang Shiao
(74) Attorney, Agent, or Firm — Foley & Lardner LLP

(57) ABSTRACT

It is to provide a tumor diagnostic agent and a tumor determination method enabling not only determination of the presence or absence of a tumor in a subject, but also determination of whether the tumor is a malignant tumor or a benign tumor, which can be used simply at low cost with reduced side effects and burden. 5-aminolevulinic acid (ALA) or its derivative, or a salt thereof is orally administered at a dose of 5 to 7 mg in terms of ALA per kg of body weight, and a urine sample 4 to 12 hours after the administration is collected. Porphyrins and creatinine in the urine sample are quantitated, and based on the value (nmol/gCre) obtained by dividing the amount of porphyrins by the amount of creatinine, a distinction among an individual without a tumor, an individual with a benign tumor, and an individual with a malignant tumor is determined. The presence or absence of a malignant tumor in a subject can be clearly determined by administering 1 to 3 mg of ALAs in terms of ALA per kg of body weight.

20 Claims, 2 Drawing Sheets

DIAGNOSTIC AGENT FOR TUMOR

CROSS-REFERENCE TO RELATED APPLICATIONS

This application is a National Stage application of PCT/JP2013/000117, filed Jan. 15, 2013, which claims priority from Japanese application JP 2012-013497, filed Jan. 25, 2012.

TECHNICAL FIELD

The present invention relates to a tumor diagnostic agent comprising a specific dose of 5-aminolevulinic acid (5-ALA) or its derivative, or a salt thereof (hereinbelow, they may be collectively referred to as "ALAs"), a method for determining the presence or absence of a tumor capable of distinguishing between malignant and benign tumors by administering a specific dose of ALAs, and a method for collecting data for the diagnosis of the presence or absence of a tumor capable of distinguishing between malignant and benign tumors.

BACKGROUND ART

In the treatment of a tumor, early detection is the most important. So far, for determination of the presence or absence of a tumor, a method for detecting a tumor marker, which is discharged from cancer cells into blood, has been widely applied. However, because most of the tumor markers are produced in a small amount also during the activity of normal cells, false positives are occasionally indicated due to chronic inflammation and the like. Even the carcinoembryonic antigen (CEA), which is known to have a relatively high positive rate, is associated with a false positive rate as high as 20%, leading to an assumption that in those who are determined to be positive by cancer screening, the probability of actually detecting cancer by a complete medical examination is as low as 1.5 to 4%. Further, in many cases early-stage cancer does not exhibit a high level of tumor marker, and thus detection sensitivity is insufficient. Furthermore, there are many types of cancer for which appropriate tumor markers have not yet been found, and a tumor marker capable of precisely covering all tumors is yet to be discovered. For the above reasons, there are many cases of false negatives, in which an individual suffering from early-stage cancer is inadvertently determined to be negative by cancer detection using a tumor marker, and the current situation is that the effectiveness of determination and diagnosis per se of the presence or absence of cancer using a cancer marker has come under question.

Meanwhile, it is known that administration of ALAs leads to the accumulation of protoporphyrin IX, which is a metabolite, in a tumor, which can be utilized for intraoperative diagnosis and treatment (see for example, Patent Documents 1 and 2). However, these methods have problems such as the necessity of preparing the isotypes of ALAs and mixing the body fluid collected (cells contained in the body fluid) with 5-ALA esters and exposing the resulting mixture to light.

Also, it has been previously assumed that increasing the dose of ALAs would result in improved diagnosability and therapeutic efficiency since the amount of porphyrin, which accumulates in a dependent manner, also increases. Hence, the only focus of discussion has been the escalation of dose also in the clinical field as well as in the field of basic research. However, it has been reported that because human cancer cells preferentially perform anaerobic metabolism, ALAs that are administered are accumulated in cancer cells as protoporphyrin IX, which is a precursor of heme and cytochrome (see for example, Patent Document 3).

It has been reported that tumor tissues can be clearly distinguished from normal tissues based on the amounts of uroporphyrin I and uroporphyrin III and their ratios in a sample collected after administration of ALAs (20 mg per kg of body weight), and there is also a report relating to a method for diagnosing the presence or absence of a tumor by analyzing porphyrins in a sample collected from inside or outside the body after administration of ALAs, such as urine (see for example, Patent Document 4). However, the above method has problems that it is very expensive because ALAs are administered at high concentrations, and even if formulation of ALAs is attempted, the amount of ALAs is too much to be capsulated, requiring ingestion of an intensely sour, strongly acidic aqueous solution. Moreover, administration of ALAs causes painful side effects such as vomiting and photosensitivity. Furthermore, a phenomenon in which the concentration of porphyrins increases also in a sample derived from a healthy individual, irrespective of the presence of a tumor, is also often observed. Accordingly, there is another concern that the above method has a critical problem as a diagnostic method in that although it is simple, it generates false positives.

PRIOR ART DOCUMENTS

Patent Documents

Patent Document 1: Japanese unexamined Patent Application Publication No. 11-12197
Patent Document 2: Japanese unexamined Patent Application Publication (Translation of PCT Application) No. 11-501914
Patent Document 3: Japanese unexamined Patent Application Publication No. 2011-016753
Patent Document 4: Japanese unexamined Patent Application Publication No. 2006-124372

SUMMARY OF THE INVENTION

Object to be Solved by the Invention

An object of the present invention is to provide a tumor diagnostic agent and a tumor determination method enabling not only determination of the presence or absence of a tumor in a subject, but also determination of whether the tumor is a malignant tumor or a benign tumor, which can be used simply at low cost with reduced side effects and burden.

Means to Solve the Object

The inventors thoroughly studied the relationship between the timing of collection of a sample, which is urine, and the optimal dose of ALAs in determination of the presence or absence of a tumor using ALAs. As a result, totally unexpectedly, they found that when ALAs were administered at a lower dose than the conventional dose, better-than-expected results can be obtained for determination of not only the presence or absence of a tumor, but also the malignancy of a tumor. That is, they found that when ALAs were administered before sleep and the first urine after wake-up in the next morning was collected, and the urinary levels of porphyrin and creatinine were measured and an operational analysis was performed using the values thus obtained, an individual without a tumor, an individual with a benign tumor, and an individual with a malignant tumor can be distinguished from one another by administering 6 mg of ALAs in terms of 5-ALA per kg of body weight, which was roughly about ¼ of the conventional dose. They further found that the presence or absence of a malignant tumor in a subject can be clearly determined by administering 2 mg of ALAs in terms of 5-ALA per kg of body weight, which was roughly about 1/12 of the conventional dose. The present invention was completed based on the foregoing findings.

That is, the present invention relates to [1] a tumor diagnostic agent comprising 5-aminolevulinic acid represented by formula (1)

(wherein $R^1$ and $R^2$ each independently represent a hydrogen atom, an alkyl group having 1 to 24 carbon atoms, an acyl group having 1 to 12 carbon atoms, an alkoxycarbonyl group having 2 to 13 carbon atoms, an aryl group having 6 to 16 carbon atoms, or an aralkyl group having 7 to 22 carbon atoms; $R^3$ represents a hydroxy group, an alkoxy group having 1 to 24 carbon atoms, an acyloxy group having 1 to 12 carbon atoms, an alkoxycarbonyloxy group having 2 to 13 carbon atoms, an aryloxy group having 6 to 16 carbon atoms, an aralkyloxy group having 7 to 22 carbon atoms, or an amino group) or its derivative, or a salt thereof, wherein a dose of oral administration is 1 to 7 mg in terms of 5-aminolevulinic acid per kg of body weight, and an amount of porphyrins is measured in a urine sample collected after the oral administration for determining a presence or absence and malignancy of a tumor, and [2] the tumor diagnostic agent according to the aforementioned [1], where the dose of the oral administration is 5 to 7 mg in terms of 5-ALA per kg of body weight.

Also, as one aspect of the present invention, the present invention relates to [3] a method for determining a presence or absence and malignancy of a tumor (hereinbelow, may also be referred to as "determination method [I]"), or for collecting data for the above determination, comprising each step of; (a) orally administering 5-ALA represented by formula (1) $R^2R^1NCH_2COCH_2CH_2COR^3$ (wherein $R^1$ and $R^2$ each independently represent a hydrogen atom, an alkyl group having 1 to 24 carbon atoms, an acyl group having 1 to 12 carbon atoms, an alkoxycarbonyl group having 2 to 13 carbon atoms, an aryl group having 6 to 16 carbon atoms, or an aralkyl group having 7 to 22 carbon atoms; $R^3$ represents a hydroxy group, an alkoxy group having 1 to 24 carbon atoms, an acyloxy group having 1 to 12 carbon atoms, an alkoxycarbonyloxy group having 2 to 13 carbon atoms, an aryloxy group having 6 to 16 carbon atoms, an aralkyloxy group having 7 to 22 carbon atoms, or an amino group) or its derivative, or a salt thereof (the ALAs of the present invention) to a subject at a dose of 5 to 7 mg in terms of 5-ALA per kg of body weight; (b) collecting a urine sample 4 to 12 hours after the administration; (c) measuring an amount of porphyrins in the urine sample, and [4] the method according to the aforementioned [3], further comprising the step of; (d) measuring an amount of creatinine in the urine sample and dividing the amount of porphyrins measured in the step (c) by the amount of creatinine to calculate a corrected value of porphyrins (nmol/gCre), and [5] the method according to the aforementioned [4], further comprising the step of; (e) determining the subject as an individual with a malignant tumor when the corrected value of porphyrins is 5000 nmol/gCre or more, determining the subject as an individual with a benign tumor when the corrected value of porphyrins is 2500 nmol/gCre or more and less than 5000 nmol/gCre, and determining the subject as an individual without a tumor when the corrected value of porphyrins is less than 2500 nmol/gCre, based on the corrected value of porphyrins.

Further, as one aspect of the present invention, the present invention relates to [6] a method for determining a presence or absence and malignancy of a tumor (hereinbelow, may also be referred to as "determination method [II]") or collecting data for the above determination, comprising each step of; (f) orally administering 5-ALA represented by formula (1) $R^2R^1NCH_2COCH_2CH_2COR^3$ (wherein $R^1$ and $R^2$ each independently represent a hydrogen atom, an alkyl group having 1 to 24 carbon atoms, an acyl group having 1 to 12 carbon atoms, an alkoxycarbonyl group having 2 to 13 carbon atoms, an aryl group having 6 to 16 carbon atoms, or an aralkyl group having 7 to 22 carbon atoms; $R^3$ represents a hydroxy group, an alkoxy group having 1 to 24 carbon atoms, an acyloxy group having 1 to 12 carbon atoms, an alkoxycarbonyloxy group having 2 to 13 carbon atoms, an aryloxy group having 6 to 16 carbon atoms, an aralkyloxy group having 7 to 22 carbon atoms, or an amino group) or its derivative, or a salt thereof (the ALAs of the present invention) to a subject at a dose of 1 to 3 mg in terms of 5-ALA per kg of body weight; (g) collecting a urine sample 4 to 12 hours after the administration; and (h) measuring an amount of porphyrins in the urine sample, and [7] the method according to the aforementioned [6], further comprising the step of; (i) measuring an amount of creatinine in the urine sample and dividing the amount of porphyrins measured in the step (h) by the amount of creatinine to calculate a corrected value of porphyrins (nmol/gCre), and [8] the method according to the aforementioned [7], further comprising the step of; (j) determining the subject as an individual with a malignant tumor when the corrected value of porphyrins is 2000 nmol/gCre or more, and determining the subject as an individual without a malignant tumor when the corrected value of porphyrins is less than 2000 nmol/gCre.

It should be noted that the determination method of the present invention is a method for assisting diagnosis by a doctor, not including the diagnostic act practiced by a doctor.

Effect of the Invention

When a specific dose of the tumor diagnostic agent of the present invention is administered, ALAs are promptly metabolized down to heme and cytochrome in normal cells. Consequently, the concentration of porphyrins discharged in urine is kept low compared to tumor cells. Accordingly, the use of the tumor diagnostic agent of the present invention rather decreases false positives owing to a reduced dose compared to the conventional dose, enabling diagnosis of the presence or absence of a tumor in a subject with a distinction between malignant and benign tumors. This makes early detection of a tumor, monitoring of therapeutic efficacy, and diagnosis of prognosis easy, and also from the viewpoint of side effects, a burden imposed on a subject can be reduced. Further, because a sample can be prepared only by ingesting the agent before sleep and collecting urine by natural urination at the time of wake-up, restraint time required for determination can be shortened and the presence or absence of a tumor can be diagnosed with a reduced burden on a subject.

MODE FOR CARRYING OUT THE INVENTION

Figure 1:
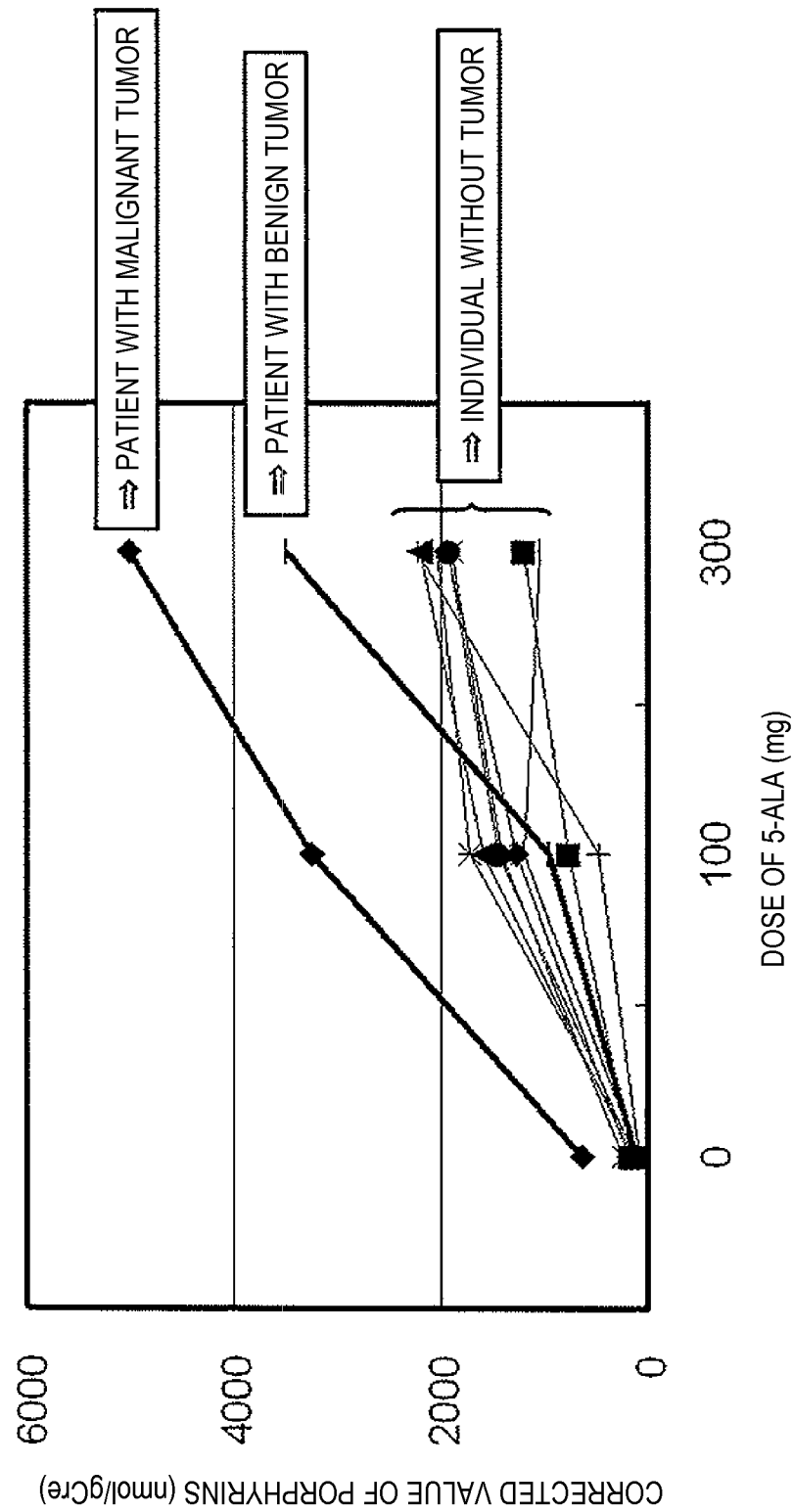
FIG. 1 is a graph illustrating the corrected values of porphyrins in urine collected from subjects who received 100 mg or 300 mg of the tumor diagnostic agent of the present invention in terms of 5-ALA.

No particular limitation is imposed on the tumor diagnostic agent of the present invention as long as it is a tumor diagnostic agent for determining the presence or absence and malignancy of a tumor by measuring the amount of porphyrins in a urine sample collected after oral administration, the tumor diagnostic agent comprising ALA represented by formula (1) $R^2R^1NCH_2COCH_2CH_2COR^3$ (wherein $R^1$ and $R^2$ each independently represent a hydrogen atom, an alkyl group having 1 to 24 carbon atoms, an acyl group having 1 to 12 carbon atoms, an alkoxycarbonyl group having 2 to 13 carbon atoms, an aryl group having 6 to 16 carbon atoms, or an aralkyl group having 7 to 22 carbon atoms; $R^3$ represents a hydroxy group, an alkoxy group having 1 to 24 carbon atoms, an acyloxy group having 1 to 12 carbon atoms, an alkoxycarbonyloxy group having 2 to 13 carbon atoms, an aryloxy group having 6 to 16 carbon atoms, an aralkyloxy group having 7 to 22 carbon atoms, or an amino group) or its derivative, or a salt thereof (the ALAs of the present invention), where the dose of the oral administration is 1 to 7 mg in terms of 5-ALA per kg body weight. The aforementioned dose of the oral administration is preferably 5 to 7 mg or 1 to 3 mg, more preferably 5 to 7 mg in terms of 5-ALA per kg body weight.

Examples of the aforementioned alkyl group having 1 to 24 carbon atoms include a linear or branched alkyl group having 1 to 24 carbon atoms, and it is preferably an alkyl group having 1 to 18 carbon atoms, particularly preferably an alkyl group having 1 to 6 carbon atoms. Specific examples of the alkyl group having 1 to 6 carbon atoms can include a methyl group, an ethyl group, an n-propyl group, an isopropyl group, an n-butyl group, a sec-butyl group, a t-butyl group, an n-pentyl group, and an n-hexyl group.

Examples of the aforementioned acyl group having 1 to 12 carbon atoms include a linear or branched alkanoyl group having 1 to 12 carbon atoms, a linear or branched alkenylcarbonyl group having 3 to 12 carbon atoms, a monocyclic or polycyclic aroyl group having 5 to 12 carbon atoms, and a monocyclic or polycyclic aryloxycarbonyl group having 5 to 12 carbon atoms. The aforementioned acyl group is particularly preferably an alkanoyl group having 1 to 6 carbon atoms, and specific examples thereof can include a formyl group, an acetyl group, a propionyl group, a butyryl group, and a pentanoyl group. It should be noted that the number of carbons in the aforementioned acyl group having 1 to 12 carbon atoms includes carbonyl carbon.

As the aforementioned alkoxycarbonyl group having 2 to 13 carbon atoms, an alkoxycarbonyl group having 2 to 7 carbon atoms is preferable, and specific examples thereof can include a methoxycarbonyl group, an ethoxycarbonyl group, an n-propoxycarbonyl group, an isopropoxycarbonyl group, a butoxycarbonyl group, a pentyloxycarbonyl group, a hexyloxycarbonyl group, a heptyloxycarbonyl group, an octyloxycarbonyl group, a nonyloxycarbonyl group, a decyloxycarbonyl group, an undecyloxycarbonyl group, and a dodecyloxycarbonyl group. It should be noted that the number of carbons in the aforementioned alkoxycarbonyl group having 2 to 13 carbon atoms includes carbonyl carbon.

Examples of the aforementioned aryl group having 6 to 16 carbon atoms include a monocyclic or polycyclic aryl group, and specific examples thereof can include a phenyl group, a naphthyl group, an anthryl group, a phenanthryl group, and a pyrenyl group.

Examples of the aforementioned aralkyl group having to 22 carbon atoms include a group consisting of the aforementioned aryl group having 6 to 16 carbon atoms and the aforementioned alkyl group having 1 to 6 carbon atoms, and specific examples thereof can include a benzyl group and a phenethyl group.

Examples of the aforementioned alkoxy group having 1 to 24 carbon atoms include a linear or branched alkoxy group having 1 to 24 carbon atoms, and it is preferably an alkoxy group having 1 to 16 carbon atoms, and particularly preferably an alkoxy group having 1 to 12 carbon atoms. Specific examples thereof can include a methoxy group, an ethoxy group, an n-propoxy group, an isopropoxy group, an n-butoxy group, a pentyloxy group, a hexyloxy group, an octyloxy group, a decyloxy group, and a dodecyloxy group.

Examples of the aforementioned acyloxy group having to 12 carbon atoms include a linear or branched alkanoyloxy group having 1 to 12 carbon atoms, and it is preferably an alkanoyloxy group having 1 to 6 carbon atoms. Specific examples thereof can include an acetoxy group, a propionyloxy group, a butyryloxy group, and a pentanoyloxy group.

As the aforementioned alkoxycarbonyloxy group having 2 to 13 carbon atoms, an alkoxycarbonyloxy group having 2 to 7 carbon atoms is preferable, and specific examples thereof can include a methoxycarbonyloxy group, an ethoxycarbonyloxy group, an n-propoxycarbonyloxy group, an isopropoxycarbonyloxy group, a butoxycarbonyloxy group, a pentyloxycarbonyloxy group, and a hexyloxycarbonyloxy group. It should be noted that the number of carbons in the aforementioned alkoxycarbonyloxy group having 2 to 13 carbon atoms includes carbonyl carbon.

Examples of the aforementioned aryloxy group having to 16 carbon atoms can include a monocyclic or polycyclic aryloxy group, and specific examples thereof can include a phenoxy group, a naphthyloxy group, an anthryloxy group, a phenanthryloxy group, and a pyrenyloxy group. As the aralkyloxy group having 7 to 22 carbon atoms, one having the aforementioned aralkyl group is preferable, and specific examples thereof can include a benzyloxy group and a phenethyloxy group.

In formula (1), $R^1$ and $R^2$ are each preferably a hydrogen atom. $R^3$ is preferably a hydroxy group, an alkoxy group, or an aralkyloxy group, more preferably a hydroxy group or an alkoxy group having 1 to 12 carbon atoms, and particularly preferably a methoxy group or a hexyloxy group.

In formula (1), a compound in which $R^1$ and $R^2$ each represent a hydrogen atom and $R^3$ represents a hydroxy group is 5-ALA, which is particularly preferable. Other than 5-ALA, preferred examples of a 5-ALA derivative include 5-ALA esters such as a 5-ALA methyl ester, a 5-ALA ethyl ester, a 5-ALA propyl ester, a 5-ALA butyl ester, a 5-ALA pentyl ester, and a 5-ALA hexyl ester. Particularly preferred examples include a 5-ALA methyl ester or a 5-ALA hexyl ester. It should be noted that 5-ALA esters are shown to exhibit similar physiological effects to 5-ALA as disclosed in, for example, Japanese unexamined Patent Application Publication (Translation of PCT Application) No. 11-501914.

Examples of a pharmacologically acceptable salt of 5-ALA or a 5-ALA derivative include a pharmacologically acceptable acid addition salt, metal salt, ammonium salt, and organic amine addition salt. Examples of the acid addition salt can include each inorganic acid salt such as hydrochloride, hydrobromide, hydroiodide, phosphate, nitrate, and sulfate, and each organic acid addition salt such as formate, acetate, propionate, toluenesulfonate, succinate, oxalate, lactate, tartrate, glycolate, methanesulfate, butyrate, valerate, citrate, fumarate, maleate, and malate. Examples of the metal salt can include each alkali metal salt such as a lithium salt, a sodium salt, and a potassium salt, each alkaline earth metal salt such as magnesium and a calcium salt, and each metal salt such as aluminum and zinc. Examples of the ammonium salt can include an ammonium salt and an alkyl ammonium salt such as a tetramethylammonium salt. Examples of the organic amine salt can include each salt such as a triethylamine salt, a piperidine salt, a morpholine salt, and a toluidine salt.

It is possible to produce 5-ALA or a 5-ALA derivative by any method of chemical synthesis, microbial production, and enzymatic production. For example, the acyl group in the amino group and the ester group in the carboxyl group of a 5-ALA derivative can be produced by acylation of the amino group or esterification of the carboxyl group by a routine method of chemical synthesis. Also, when acquisition of a salt of 5-ALA or 5-ALA derivative is desired, the compound represented by formula (1) can be directly purified when it is obtained in the form of a salt, while when the compound represented by formula (1) is obtained in the free form, a salt may be formed by a common method by dissolving or suspending it in an appropriate organic solvent and adding an acid or a base thereto. The ALAs of the present invention may be present in the form of adducts with water or various kinds of solvents, and these adducts can also be used as the tumor diagnostic agent of the present invention.

As the tumor diagnostic agent of the present invention, an appropriate combination of two or more of the ALAs of the present invention can be used. For example, 5-ALA, a variety of 5-ALA esters such as a 5-ALA methyl ester, a 5-ALA ethyl ester, a 5-ALA propyl ester, a 5-ALA butyl ester, and a 5-ALA pentyl ester, and hydrochloride, phosphate, sulfate, and the like of the above 5-ALA and 5-ALA esters can be used singly or in combination of two or more of them.

The ALAs of the present invention can be provided as appropriate preparations by a routine method. As the dosage form of the preparation, it may be a solid preparation such as a powder and a granule; however, from the viewpoint of easy application, it is preferably prepared as a liquid agent such as a solution, an emulsion, and a suspension. Preferred examples of the production method for the aforementioned liquid agent include a method for mixing the ALAs of the present invention with a solvent, and a method for further mixing with a suspending agent and an emulsifying agent. As shown above, when the ALAs of the present invention are provided as preparations, an arbitrary component such as an appropriate carrier, for example an excipient, a binder, a solvent, a solubilizing aid, a suspending agent, an emulsifying agent, an isotonizing agent, a buffer, a stabilizer, a pain-killing agent, a preservative, an antioxidant, a coloring agent, a lubricant, a disintegrant, a humectant, an adsorbent, a sweetener, and a diluent, can be added as required for formulation.

Of the methods for determining the presence or absence and malignancy of a tumor according to the present invention, the aforementioned determination method [I] is characterized in that the presence or absence and malignancy of a tumor is determined by orally administering the ALAs of the present invention to a subject at a dose of 5 to 7 mg in terms of 5-ALA per kg body weight, while the aforementioned determination method [II] is characterized in that the presence or absence of a malignant tumor is determined by orally administering the ALAs of the present invention to a subject at a dose of 1 to 3 mg in terms of 5-ALA per kg body weight.

The step (a) in the determination method [I] is a step of orally administering the ALAs of the present invention to a subject at a dose of 5 to 7 mg in terms of 5-ALA per kg body weight. As to the timing of administration, administration before sleep is desirable because urine can be collected at the time of wake-up, thereby reducing a burden on a subject.

The step (b) in the determination method [I] is a step of collecting a urine sample 4 to 12 hours after the administration of the ALAs of the present invention. Examples of the aforementioned urine sample 4 to 12 hours after the administration can include a "natural urine sample" or a "urine sample collected by a catheter and the like", both of which are collected at any time within a time frame of 4 to 12 hours after the administration of the ALAs of the present invention. The aforementioned collection may be performed once or multiple times, and considering a reduced burden on a subject, it is preferable to administer the ALAs of the present invention before sleep and collect a urine sample by natural urination at the time of wake-up. Because the urinary porphyrins are susceptible to light and temperature, it is preferable to measure the amount of porphyrins right after collection. When porphyrins are not measured right after collection, the sample is preferably stored under lightproof conditions, and the storage temperature is preferably 1 to 25° C., more preferably 2 to 10° C., among which 4° C. is particularly preferable. Also, it is preferable to measure the amounts of porphyrins and creatinine at the same time.

The step (c) in the determination method [I] is a step of measuring the amount of porphyrins in the urine sample. Examples of porphyrin(s) measured according to the present invention can include protoporphyrin IX, uroporphyrin I, uroporphyrin III, coporphyrin I, coporphyrin III, heptacarboxyl porphyrin I, heptacarboxyl porphyrin III, hexacarboxyl porphyrin I, hexacarboxyl porphyrin III, pentacarboxyl porphyrin I, pentacarboxyl porphyrin III, isocoproporphyrin, harderoporphyrin, isoharderoporphyrin, mesoporphyrin IX, deuteroporphyrin IX, and pemptoporphyrin. Among them, preferred examples can include protoporphyrin IX, uroporphyrin I, uroporphyrin III, coporphyrin I, and coporphyrin III.

A method for measuring the aforementioned amount of porphyrins is not particularly limited as long as it is a method capable of quantitating porphyrins. The method can be appropriately selected according to the purpose and convenience, and measurement can be performed by a method such as high-performance liquid chromatography (HPLC), thin layer chromatography (TLC), an HPLC fluorescence detection method using a fluorescence detector, and a biological detection method such as immunoassay, among which an HPLC fluorescence detection method is particularly preferable.

In the aforementioned HPLC fluorescence detection method, porphyrins can be detected at an excitation wavelength of 350 to 500 nm and a fluorescence wavelength of 550 to 750 nm, preferably at an excitation wavelength of 380 to 440 nm and a fluorescence wavelength of 590 to 690 nm, and more preferably at an excitation wavelength of 400 to 410 nm and a fluorescence wavelength of 610 to 640 nm. Specifically, a method comprising adding an iodine-acetic acid mixed solution (1/1, v/v) to 200 µL of a test urine sample; mixing the resulting solution by vortex; subjecting the resulting mixture to centrifugation for 10 minutes at 10000 rpm; injecting 20 μL of the supernatant thus collected into an HPLC apparatus and performing measurement at a flow rate of 1.0 mL/min and a column temperature of 40° C.; and calculating the concentration of porphyrins using a fluorescence detector, can be given as an example.

The aforementioned determination method [I] preferably further comprises the aforementioned step of (d) measuring the amount of creatinine in the urine sample and dividing the amount of porphyrins measured by the step (c) by the amount of creatinine to calculate a corrected value of porphyrins (nmol/gCre). Because the concentration of water in urine greatly fluctuates due to the effect of physiological variables such as the presence or absence of food intake, ingestion of a large/small amount of water, and a large/small amount of perspiration, there is a possibility that evaluation of the amount of porphyrins only based on the component concentration may lead to underestimation or overestimation. In light of the above, correction of concentration is needed. As a method of this correction, a method comprising simultaneously measuring the urinary components and urine volume and performing correction by calculating the volume of urination in a day, and a method comprising correcting the concentration of the component of interest by simultaneously quantitating the urinary components and a substance whose amount in urine fluctuates very little, which serves as the standard, are known. When a substance serving as the standard is used, creatinine is widely employed. Creatinine is reabsorbed in a small amount by the renal tubules in the process of discharge from the kidney and present in a relatively large amount without being influenced by physiological variables, and the amount of creatinine produced in an adult is perceived to be substantially constant per kg body weight. Specifically, determination can be performed based on the corrected value of porphyrins (nmol/gCre), which has been subjected to so-called "creatinine correction", by measuring the amount of creatinine in the urine sample used in the present invention and dividing the amount of porphyrins measured by the aforementioned step (c) by the amount of creatinine. It is to be noted that, as a method for measuring the amount of creatinine in a urine sample, an already established method such as the Jaffe's method and the enzyme method (creatinase-sarcosine oxidase-POD method) can be employed, and the enzyme method is generally employed, for which a large number of highly sensitive kits are commercially available.

The aforementioned determination method [I] preferably further comprises the aforementioned step of (e) determining, based on the corrected value of porphyrins calculated by the aforementioned step (d), the presence or absence and malignancy of a tumor. In this method, in comparison with the corrected value of porphyrins in a negative control urine sample obtained from an individual without a tumor, when the corrected value of porphyrins in a subject is remarkably significantly higher, the subject can be determined to be an individual with a malignant tumor, and when the corrected value of porphyrins in a subject is significantly higher, the subject can be determined to be an individual with a benign tumor, and when there is no significant difference, the subject can be determined to be an individual without a tumor. Specifically, based on the corrected value of porphyrins, when it is 5000 nmol/gCre or more, the subject can be determined to be an individual with a malignant tumor, and when it is 2500 nmol/gCre or more and less than 5000 nmol/gCre, the subject can be determined to be an individual with a benign tumor, and when it is less than 2500 nmol/gCre, the subject can be determined to be an individual without a tumor.

In the determination method [II], except for orally administering the ALAs of the present invention to a subject at a dose of 1 to 3 mg in terms of 5-ALA per kg body weight in the step (f), the steps (g) to (i) performed subsequent to the step (f) correspond to the steps (b) to (d) in the aforementioned determination method [I], respectively, and thus the steps (g) to (i) can be performed in accordance with the steps (b) to (d).

The determination method [II] preferably further comprises the aforementioned step of (j) determining the presence or absence and malignancy of a tumor based on the corrected value of porphyrins calculated by the aforementioned step (i). In this method, in comparison with the corrected value of porphyrins in a negative control urine sample obtained from an individual without a tumor, when the corrected value of porphyrins in a subject is significantly higher, the subject can be determined to be an individual with a malignant tumor, and when there is no significant difference, the subject can be determined to be an individual without a malignant tumor, who is not an individual with a malignant tumor. Specifically, based on the corrected value of porphyrins, when it is 2000 nmol/gCre or more, the subject can be determined to be an individual with a malignant tumor, and when it is less than 2000 nmol/gCre, the subject can be determined to be an individual with a benign tumor or an individual without a tumor.

In the determination method [II], a subject who has been determined to be an individual without a malignant tumor by the aforementioned step (j) can further be subjected to determination by the aforementioned determination method [I]. That is, the subject can be determined to be an individual with a benign tumor or an individual without a tumor based on the corrected value of porphyrins in a urine sample collected 4 to 12 hours after oral administration of 5 to 7 mg of ALAs in terms of ALA per kg body weight.

As the method for collecting data for determination of the presence or absence and malignancy of a tumor according to the present invention, a method comprising each of the steps of 1) orally administering the aforementioned tumor diagnostic agent to a subject at a dose of 5 to 7 mg or 1 to 3 mg in terms of 5-ALA per kg body weight; 2) collecting a urine sample 4 to 12 hours after the administration; 3) measuring the amount of porphyrins in the urine sample; and 4) measuring the amount of creatinine in the urine sample and dividing the amount of porphyrins measured by the step 3) by the amount of creatinine to calculate a corrected value of porphyrins (nmol/gCre) can be given as an example.

Tumors to which the tumor diagnostic agent, the determination method, and the method for collecting data for determination according to the present invention are applied can be roughly classified into a malignant tumor and a benign tumor. Examples of a malignant tumor, which is observed to be infiltrative and metastatic, can include a cancer caused by malignant transformation of the epithelial cells such as melanocarcinoma (melanoma), skin cancer, lung cancer, trachea and bronchus cancer, oral epithelial cancer, esophageal cancer, stomach cancer, colon cancer, rectal cancer, colorectal cancer, liver and intrahepatic bile duct cancer, renal cancer, pancreatic cancer, prostate cancer, breast cancer, uterine cancer, ovarian cancer, and a brain tumor; namely, cancer and a tumor caused by malignant transformation of the constituent cells of supporting tissues such as a malignant tumor, osteosarcoma, and myosarcoma. Meanwhile, examples of a benign tumor, which proliferates autonomously but only at the site where it is generated, can include a tumor generated from epithelial cells such as papilloma, adenoma, and cystadenoma and a tumor generated from non-epithelial cells such as fibroma, myxoma, lipoma, chondroma, osteoma, rhabdomyoma, leiomyoma, and angioma. Although a tissue in which a malignant tumor or a benign tumor is present is not particularly limited, examples thereof can include the brain, eye, nasal passage, nasal cavity, trachea, bronchium, oral cavity, pharynx, esophagus, stomach, breast, colon and rectum, lung, ovary, central nervous system, liver, bladder, urethra, urinary duct, pancreas, cervical canal, abdominal cavity, anus, uterine cervix, genital, kidney, prostate gland, muscle, bone, and hematopoietic cells.

Hereinbelow, the present invention will be more specifically described with reference to Examples; however, the technical scope of the present invention is not limited to the examples shown below.

EXAMPLES

A total of eight individuals including seven healthy volunteers in whom no particular abnormality was found by health examination and the like and one volunteer with a malignant tumor, who was given a diagnosis of cancer by a doctor, were studied. The average body weight of the volunteers was 50 kg. The volunteers were instructed to ingest one capsule encapsulating 100 mg of 5-ALA before sleep and collect the first urine at the time of wake-up. Also, they were instructed to ingest, on another day, three capsules, each encapsulating 100 mg of 5-ALA, before sleep and collect the first urine at the time of wake-up.

To 200 μL of the urine samples thus collected, 200 μL of a 0.08% iodine-acetic acid mixed solution (1/1, v/v) was added, followed by vortex mixing and 10 minutes of centrifugation at 10000 rpm at 4° C. The supernatants of the centrifuged solutions were collected and then each ingested in an HPLC apparatus (Shimadzu LC-10A VP) in an amount of 20 μL. As the column, a CAPCELL PAK C18 AG120 (4.6 mm×250 mm, 5 μm, the product of Shimadzu GLC, Ltd.) was used. As the mobile phase, A: 12.5% acetonitrile, 1M ammonium acetate (pH 5.15) and B: 80% acetonitrile, 50 mM ammonium acetate (pH 5.15) were used, and the following system of gradient was set: 0 to 5 minutes isocratic A 100%; 5 to 30 minutes linear gradient A 100 to 0%, B 0 to 100%; 30 to 40 minutes isocratic B 100%; 40 to 41 minutes linear gradient A 0 to 100%, B 100 to 0%; and 41 to 50 minutes isocratic A 100%. Measurement was performed at a flow rate of 1.0 mL/min and a column temperature of 40° C. The detection wavelength was set at an excitation wavelength (Ex) of 404 nm and a fluorescence wavelength (Em) of 620 nm.

The production of a calibration curve by the internal standard method using a separately prepared standard solution and data processing such as calculation of the results of quantitation were carried out using an LC-solution (Version 1.21 SP1) (the product of Shimadzu Corporation). The concentration of each porphyrin in each sample was calculated from the peak area of the standard solution, and the amount of porphyrins was obtained as the sum of the amounts of uroporphyrins I and III and coproporphyrins I and III in urine.

Using the same urine samples, the amount of creatinine was also measured by the enzyme method using a CicaLiquid-S CRE (the product of Kanto Chemical Co., Inc.) as the reagent and an automated analyzer JCA-BM12 (the product of JEOL, Ltd) as the measuring apparatus, and corrected values of porphyrins were calculated. Also, as a control, the amounts of porphyrins and creatinine in a urine sample obtained from each volunteer were measured when 5-ALA was not administered and corrected values of porphyrins were calculated. The results are shown in FIG. 1.

(Results)

In FIG. 1, the dose of 5-ALA ingested was plotted on the X-axis and the values obtained by dividing the amount of measured porphyrins by the amount of creatinine was plotted on the Y-axis as the corrected value of urinary porphyrins (nmol/gCre). When 300 mg of 5-ALA was administered to the aforementioned eight individuals, the value of the urinary concentration of porphyrin of an individual with a malignant tumor was found to exceed 5000 nmol/gCre. Although the values of the urinary concentrations of porphyrins of six healthy volunteers were less than 2500 nmol/gCre, the value of the urinary concentration of porphyrin of the remaining one healthy volunteer was about 3500 nmol/gCre. After the above study, this subject had a complete medical check-up by consulting a doctor. As a result, uterine fibroid was found, revealing that she was an individual with a benign tumor.

Meanwhile, when 100 mg of 5-ALA was administered, the value of the urinary concentration of porphyrin of an individual with a malignant tumor was found to exceed 3000 nmol/gCre, which was significantly higher than the values of the seven healthy volunteers. Accordingly, it was confirmed that an individual with a malignant tumor and an individual other than those who with a malignant tumor can be clearly distinguished from each other by administering 5-ALA at 2 mg/kg body weight.

From the above results, it was shown that administration at a dose of 300 mg can distinguish between not only the presence and absence of a tumor, but also a malignant tumor and a benign tumor. Also, it was shown that a malignant tumor can be detected by administering 100 mg of 5-ALA. It should be noted that neither stomach discomfort nor nausea was observed in all of the individuals given 5-ALA.

Comparative Example

Figure 2:
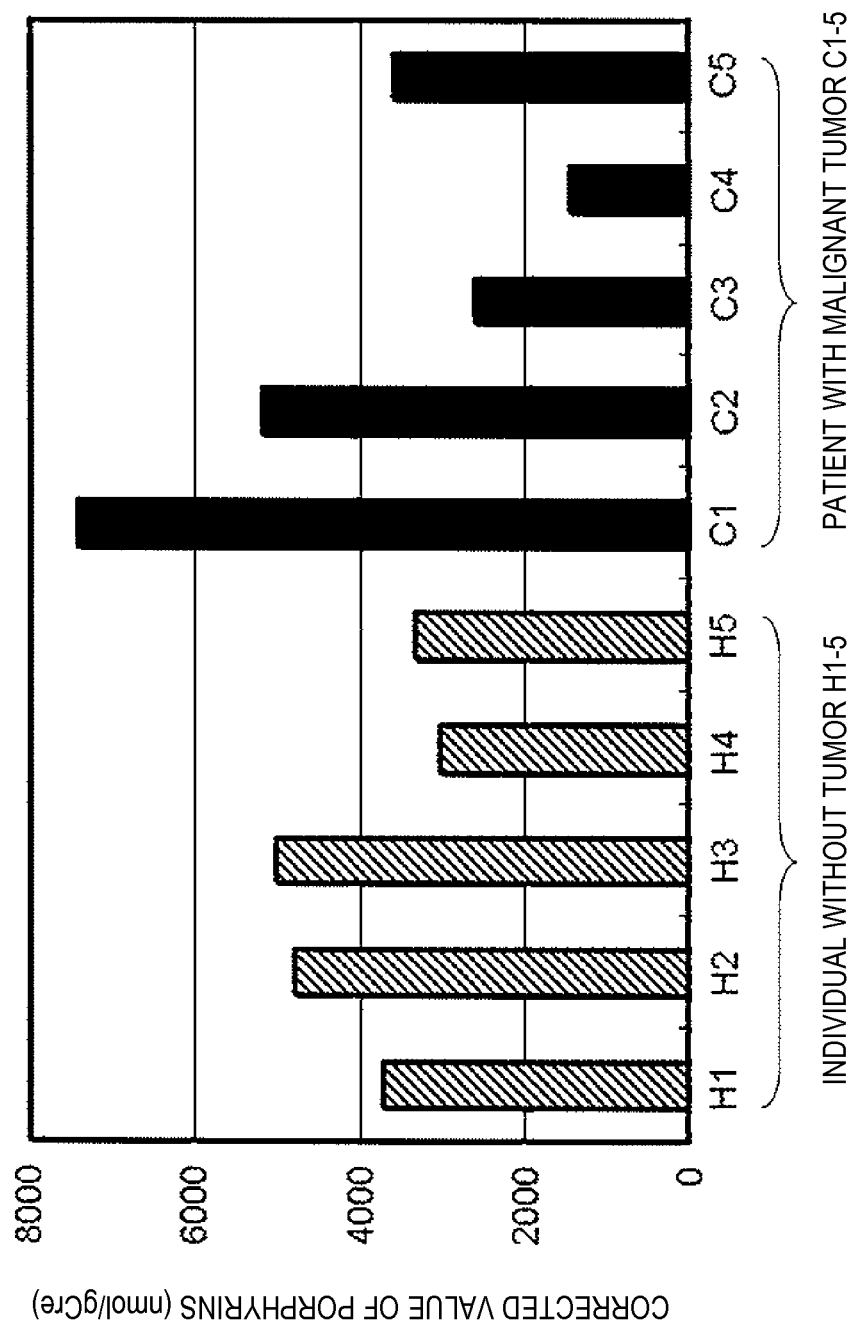
FIG. 2 is a graph illustrating the corrected values of porphyrins in urine collected from subjects who received 1 g of the tumor diagnostic agent of the present invention in terms of 5-ALA.

A total of 10 individuals including five healthy volunteers in whom no particular abnormality was found by health examination and the like and five volunteers with a malignant tumor, who were given a diagnosis of cancer by a doctor, ingested 1 g of 5-ALA. Spot urine was collected at 0 h, 4 h, and 8 h after ingestion, and in each urine collected, a corrected value of porphyrins (nmol/gCre) was calculated and the sum of the amounts of uroporphyrins I and III and coproporphyrins I and III in spot urine collected at 0 h, 4 h, and 8 h after ingestion was used as the corrected value of porphyrins of each individual. The results are shown in FIG. 2. As a result, individuals without a tumor (H1 to H5) and individuals with a malignant tumor (C1 to C5) could not be clearly distinguished from each other. The above data are results indicating that ingestion of 5-ALA at a concentration as high as 1 g, which was the conventionally, generally used dose, led to the appearance of false positives, verifying that the optimization of dose according to the present invention was excellent. Further, some of the volunteers developed stomach discomfort and nausea.

The invention claimed is:

1. A method for diagnosing a tumor comprising the following steps (a) and (b);
   (a) orally administering a compound represented by formula (1)

$R^2R^1NCH_2COCH_2CH_2COR^3$, wherein $R^1$ and $R^2$ each independently represent a hydrogen atom, an alkyl group having 1 to 24 carbon atoms, an acyl group having 1 to 12 carbon atoms, an alkoxycarbonyl group having 2 to 13 carbon atoms, an aryl group having 6 to 16 carbon atoms, or an aralkyl group having 7 to 22 carbon atoms; $R^3$ represents a hydroxy group, an alkoxy group having 1 to 24 carbon atoms, an acyloxy group having 1 to 12 carbon atoms, an alkoxycarbonyloxy group having 2 to 13 carbon atoms, an aryloxy group having 6 to 16 carbon atoms, an aralkyloxy group having 7 to 22 carbon atoms, or an amino group, or a salt thereof to a subject at a dose of 1 to 7 mg of the compound represented by formula (1) per kg of body weight; and (b) measuring an amount of porphyrins in a urine sample collected from the subject after the oral administration to determine a presence or absence and malignancy of a tumor.

2. The method for diagnosing a tumor according to claim 1, wherein the dose of the oral administration is 5 to 7 mg in terms of 5-aminolevulinic acid per kg of body weight.

3. The method for diagnosing a tumor according to claim 2, further comprising the following step (c);

(c) measuring an amount of creatinine in the urine sample and dividing the amount of porphyrins measured in the step (b) by the amount of creatinine to calculate a corrected value of porphyrins (nmol/gCre).

4. The method for diagnosing a tumor according to claim 3, further comprising the following step (d);

(d) determining the subject as an individual with a malignant tumor when the corrected value of porphyrins is 5000 nmol/gCre or more, determining the subject as an individual with a benign tumor when the corrected value of porphyrins is 2500 nmol/gCre or more and less than 5000 nmol/gCre, and determining the subject as an individual without a tumor when the corrected value of porphyrins is less than 2500 nmol/gCre, based on the corrected value of porphyrins.

5. The method for diagnosing a tumor according to claim 1, wherein the dose of the oral administration is 1 to 3 mg in terms of 5-aminolevulinic acid per kg of body weight.

6. The method for diagnosing a tumor according to claim 5, further comprising the following step (e);

(e) measuring an amount of creatinine in the urine sample and dividing the amount of porphyrins measured in the step (b) by the amount of creatinine to calculate a corrected value of porphyrins (nmol/gCre).

7. The method for diagnosing a tumor according to claim 6, further comprising the following step (f);

(f) determining the subject as an individual with a malignant tumor when the corrected value of porphyrins is 2000 nmol/gCre or more, and determining the subject as an individual without a malignant tumor when the corrected value of porphyrins is less than 2000 nmol/gCre.

8. The method for diagnosing a tumor according to claim 1, wherein the collected urine sample is a urine sample 4 to 12 hours after the administration in the step (b).

9. The method for diagnosing a tumor according to claim 2, wherein the collected urine sample is a urine sample 4 to 12 hours after the administration in the step (b).

10. The method for diagnosing a tumor according to claim 3, wherein the collected urine sample is a urine sample 4 to 12 hours after the administration in the step (b).

11. The method for diagnosing a tumor according to claim 4, wherein the collected urine sample is a urine sample 4 to 12 hours after the administration in the step (b).

12. The method for diagnosing a tumor according to claim 5, wherein the collected urine sample is a urine sample 4 to 12 hours after the administration in the step (b).

13. The method for diagnosing a tumor according to claim 6, wherein the collected urine sample is a urine sample 4 to 12 hours after the administration in the step (b).

14. The method for diagnosing a tumor according to claim 7, wherein the collected urine sample is a urine sample 4 to 12 hours after the administration in the step (b).

15. The method for diagnosing a tumor according to claim 1, wherein the collected urine sample is a urine sample by natural urination in the step (b).

16. The method for diagnosing a tumor according to claim 2, wherein the collected urine sample is a urine sample by natural urination in the step (b).

17. The method for diagnosing a tumor according to claim 4, wherein the collected urine sample is a urine sample by natural urination in the step (b).

18. The method for diagnosing a tumor according to claim 5, wherein the collected urine sample is a urine sample by natural urination in the step (b).

19. The method for diagnosing a tumor according to claim 7, wherein the collected urine sample is a urine sample by natural urination in the step (b).

20. The method for diagnosing a tumor according to claim 1, wherein the compound represented by formula (1) is 5-aminolevulinic acid.

* * * * *